United States Patent [19]

Curlee

[11] Patent Number: 4,756,306
[45] Date of Patent: * Jul. 12, 1988

[54] THERAPEUTIC BELT

[75] Inventor: James D. Curlee, Mechanicsburg, Pa.

[73] Assignee: Safeguard Technologies, Inc., Leesport, Pa.

[*] Notice: The portion of the term of this patent subsequent to Nov. 18, 2003 has been disclaimed.

[21] Appl. No.: 826,307

[22] Filed: Feb. 5, 1986

Related U.S. Application Data

[63] Continuation-in-part of Ser. No. 591,501, Mar. 20, 1984, abandoned.

[51] Int. Cl.$^4$ ............................. A61F 5/03; A61F 5/34
[52] U.S. Cl. ................................. 128/78; 128/DIG. 20
[58] Field of Search ................. 128/78, 75, 69, 82, 128/84 R, 89 R, DIG. 20

[56] References Cited

U.S. PATENT DOCUMENTS

| 1,646,590 | 10/1927 | Mildenberg | 128/78 |
|---|---|---|---|
| 2,104,758 | 1/1938 | Poppen | 128/DIG. 20 |
| 2,240,308 | 4/1941 | Mahe | 128/96 |
| 2,554,337 | 5/1951 | Lampart | 128/69 |
| 3,017,133 | 1/1963 | Eisen | 128/78 |
| 3,521,623 | 7/1970 | Nichols et al. | 128/DIG. 20 |
| 3,955,565 | 5/1976 | Johnson, Jr. | 128/89 R |
| 3,974,827 | 8/1976 | Bodeen | 128/DIG. 20 |
| 4,135,503 | 1/1979 | Ramano | 128/78 |
| 4,175,548 | 11/1979 | Henry | 128/78 |
| 4,178,922 | 12/1979 | Curlee | 128/78 |
| 4,178,923 | 12/1979 | Curlee | 128/78 |
| 4,475,543 | 10/1984 | Brooks et al. | 128/89 R |
| 4,552,135 | 11/1985 | Racz et al. | 128/78 |
| 4,559,933 | 12/1985 | Batard et al. | 128/78 |
| 4,576,145 | 3/1986 | Hyman et al. | 128/78 |
| 4,597,386 | 7/1986 | Goldstein | 128/78 |
| 4,622,957 | 11/1986 | Curlee | 128/78 |
| 4,682,587 | 7/1987 | Curlee | 128/78 |
| 4,682,588 | 7/1987 | Curlee | 128/78 |

FOREIGN PATENT DOCUMENTS

| 2454702 | 5/1976 | Fed. Rep. of Germany | 128/78 |
|---|---|---|---|
| 1461408 | 11/1966 | France | 128/78 |
| 985591 | 3/1965 | United Kingdom | 128/DIG. 20 |

Primary Examiner—Edgar S. Burr
Assistant Examiner—Tonya Lamb
Attorney, Agent, or Firm—Wenderoth, Lind & Ponack

[57] ABSTRACT

An improved therapeutic belt which is peculiarly adapted for the sacro-lumbar region of the body is disclosed. The belt appliance, in essence, is comprised of an elongated support surface formed from material that is bendable when subjected to forces encountered thereby; a flexible cover disposed on said support surface secured thereto along its edges, thereby forming an envelope; a source of fluid; a means introducing said fluid into said envelope for inflating and retaining said fluid, causing said surface to bend to assume a predetermined curvature, which is preferably in the shape of a crescent; and a means removably securing the free ends of said support surface.

13 Claims, 3 Drawing Sheets

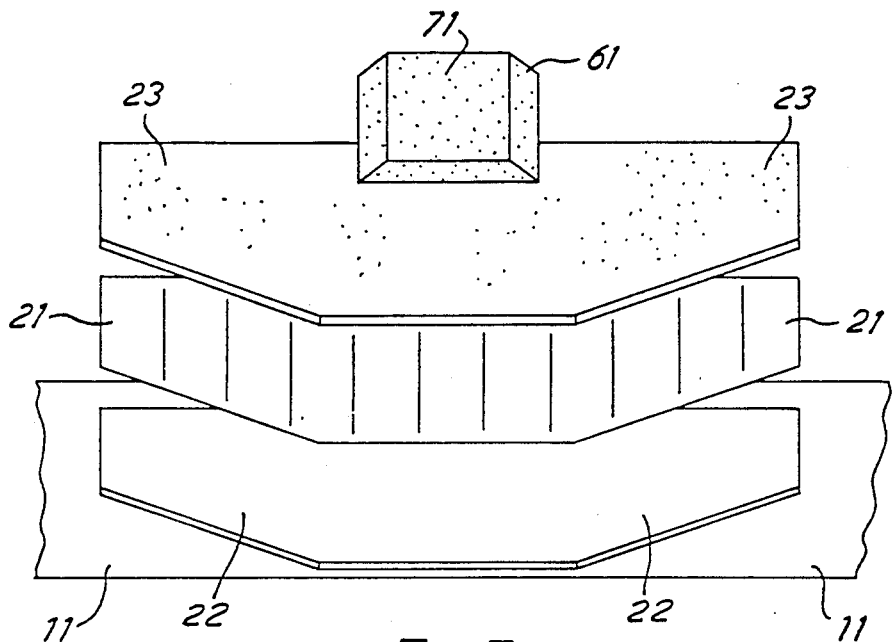
Fig. 5
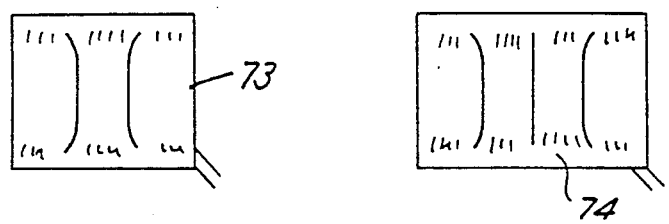
Fig. 6
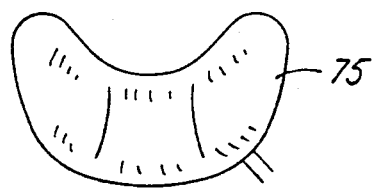

THERAPEUTIC BELT

This application is a continuation in part of pending Ser. No. 591,501 filed Mar. 20, 1984, now abandoned.

FIELD OF THE INVENTION

The present invention relates generally to therapeutic devices and more particularly to a corset appliance which may be applied to the sacro-lumbar region of the human body in order to prevent or treat injuries to the aforestated region.

BACKGROUND OF THE INVENTION

As is well known, the human vertibrae or spinal column is comprised of seven cervical vertebrae, twelve thoracic vertebrae, and five lumbar vertebrae. The vertebrae are disposed in a stacked array and interposed between the same are fibrocartilages or discs. Thirty-one pairs of spinal nerves are also associated with the spinal column, and the nerves are sometimes adversely affected by means of the relative disposition of one or more vertebrae whereby severe pain results. For example, an accident, fall, uneven stress, tension, over-exertion, or the like, can cause a minor displacement or misalignment of one or more of the vertebrae which, in turn, can cause pressure to be exerted upon spinal nerve roots.

It has additionally been found that if the particular misaligned vertebrae is re-aligned in conjunction with the residual, properly aligned vertebrae, the pressure upon the spinal nerves is alleviated and, consequently, the pain suffered by the person is relieved. The re-alignment of the misaligned vertebrae is normally accomplished as a result of pressure being applied to the particularly afflicted areas of the body, and in accordance with these principles, prior art therapeutic appliances have been developed in order to provide such counterpressure to the affected body regions.

Prior art appliances of the aforenoted type are exemplified by those disclosed in U.S. Pat. No. 4,178,922 (J. D. Curlee) and French Patent No. 1,461,408 (M. Gross) These appliances include an inflatable bladder means which seeks to exert counterpressure at a precise body location as a result of the inflated expansion thereof. It has been found, however, that such appliances, and, in particular, U.S. Pat. No. 4,178,922, while exerting the desired counterpressure at the precise body locations, do not and cannot, in fact, provide an effective and comfortable support to the entire muscle mass related to the lumbar region of the lower back. This is particularly characteristic of appliances applied to the posterior lumbar region of the body, where, due to the necessity of providing specific counterpressure to a precise spinal location, by means such as an inflated bladder, such prior art appliances have been unable to provide simultaneous deliberate and comfortable counterpressure and support to the muscle mass connected with the lumbar region.

In the early devices made by the inventor, described in U.S. Pat. Nos. 4,178,922 and 4,178,923, the devices were limited commercially and therapeutically by their structure and ability to conform to the human body. For example, the air pockets of the early Curlee patents were generally pocketed in shape, as opposed to the present invention's corrugated configuration. The present invention is finally crescent shaped when inflated and more adequately conforms to the contours of the body. See FIG. 1 for an illustration of the improved elements which constitute the present invention. It is evident further that the original Curlee patents were restricted to use by people in a work environment.

Thus, the present invention involves a tapering corrugated inflation strip with spaced-agent air-tight envelopes attached to a rigid or semi-rigid backing. The tapering is designed so that the belt clears the ribs and iliac crests. The manner in which the air pockets or bladder is attached to the semi-rigid membrane controls the application of pressure to specific points along the lumbar region.

Further, when such prior art appliances such as Gross, above, are normally employed, adequate contact and pressurization of the afflicted body region is attempted to be accomplished by means of increased tightening of the appliance about the wearer's body or increasing the degree of pressurization of the bladder generally. Such modes of practice can be dangerous in that other portions of the body are deleteriously affected. Particularly, where increased tightening of the appliance is attempted to effect greater pressurization of the afflicted body region, such tightening serves to dangerously constrict the cardio-vascular network of the body and generally provides increased discomfort to the wearer.

Similarly, as a result of elastic properties in the case of bladder devices, wherein bladders have a high coefficient of stretchability, as the pressure therein is increased, the contact area defined between the bladder and the body is increased and the cardiovascular network of the body is severely constricted in a manner similar to that accomplished by means of a conventional blood pressure cuff. Prolonged usage of such appliances can result in major complications, such as, for example, renal isclemia, muscle spasms, or arteriosclerosis-related problems.

Still further, in the case of such prior art appliances utilizing individual longitudinal air cell pockets of material exhibiting a low coefficient of stretchability, adequate contact and counterpressure at precise body locations is accomplished and maintained without the threat of constricting the body's cardiovascular network, but at the expense of failing to provide a more generalized and effective support to the muscle structure of the lower back region related to the sacro-lumbar region of the spinal column.

OBJECTS OF THE INVENTION

Accordingly, it is an object of the present invention to provide a new and improved therapeutic appliance.

Another object of the present invention is to provide a new and improved therapeutic appliance which is adapted to be applied to the lumbar region of the human back in order to relieve or prevent the occurrence of lower back pain afflictions.

Still another object of the present invention is to provide a new and improved therapeutic appliance for relieving or preventing the occurrence of pain within the sacro-lumbar region of the human back and which overcomes the various disadvantages characteristic of prior art appliances.

Yet another object of the present invention is to provide a new and improved therapeutic appliance which is adapted to be applied to the sacro-lumbar region of the human back in order to apply precisely localized counter-pressure to specific areas of the aforenoted back region.

Still yet another object of the present invention is to provide a new and improved therapeutic appliance adapted to be applied to the sacro-lumbar region of the back which is capable of applying supportive counterpressure to the muscle structure of the lower back generally, while providing localized counterpressure to specific areas of the aforenoted back region.

A further object of the present invention is to provide a new and improved therapeutic appliance extending in a lateral direction which employs a plurality of longitudinally extending, laterally spaced inflatable air cells mounted on a rigid or semi-rigid backing wherein padding can be applied at various positions to "fill" contours of the back and insure total contact with the aforementioned region.

A still further object of the present invention is to provide a new and improved therapeutic appliance adapted to be applied to the sacro-lumbar region of the back which is tapered so as not to interfere with the wearer's hip region or ribcage to provide maximum comfort and concentrate pressure more directly against back muscles.

A still further object of the present invention is to provide a new and improved therapeutic appliance which can be simply, easily, and economically manufactured by means of mass production techniques.

SUMMARY OF THE INVENTION

The foregoing and other objectives are achieved in accordance with the present invention through the provision of a therapeutic belt appliance consisting of an inflatable air bladder, support surface, padding means, and lining. The air bladder of the appliance is directed into at least two intercommunicating cells, which, in its preferred embodiment are arranged as multiple ribs in a nesting parallel configuration perpendicular to the axis of a belting means which secures the device to the wearer. A means of introducing fluid into said bladder is utilized for inflating same, and means causing said support surface to bendably assume a predetermined curvature or crescent of no less than 30°. The lining means is disposed to surround the bladder, padding, and support surface to form an integrated unit. The support surface has an attachment means which permits the attachment of the support unit to a belting material as a means for securing the device to the wearer. Disposed upon the free ends of said belting material are means removably securing said unit. Additional padding material may be applied to the therapeutic belt on the side next to the user to cushion and provide additional directed counterpressure to specfic areas of the sacro-lumbar area. Padding may also be disposed wrapped around the top of the inflatable unit and the unit itself may be contoured and narrowed in width along its end to avoid the hip area of the user.

DESCRIPTION OF THE FIGURES

Various additional objects, features and advantages of the invention will be better understood from the following description when considered in conjunction with the accompanying figures, to wit:

FIG. 5 is an expanded view of the inflatable support unit with optional padding; and FIG. 6 is a perspective view of additional embodiments of optional inflatable padding means.

DESCRIPTION OF THE PREFERRED EMBODIMENTS

Figure 1:
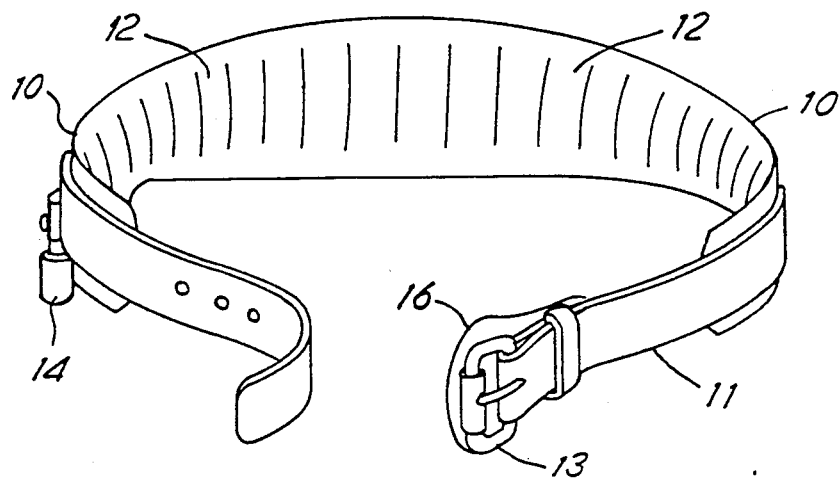
FIG. 1 is a perspective view of the improved therapeutic belt appliance.

The improved therapeutic belt appliance of the present invention is generally disclosed in FIG. 1 wherein the therapeutic belt 10 is shown. The therapeutic belt 10 extends in a lateral direction and includes belting material 11 which can be made of leather or any material suitable for wrapping around the waist. Secured to the belting material 11 is inflatable support padding means 12. Said padding 12 is secured to the belting material 11 on the side closest to the wearer. The padding 12 may be slightly wider than the belting material 11 in order to provide additional comfort to the wearer. The belting material is fitted with a fastening means 13, such as a buckle or the like, capable of securing said belt about the wearer. An inflation device 14 can be attached to the outside of the belt 11 by any means capable of holding it in position. The preferred method of attaching said inflation device is by means of a "C" ring clip holder consisting of a spring clasp made of suitable plastic, steel or other suitable material as in FIG. 4.

Figure 2:
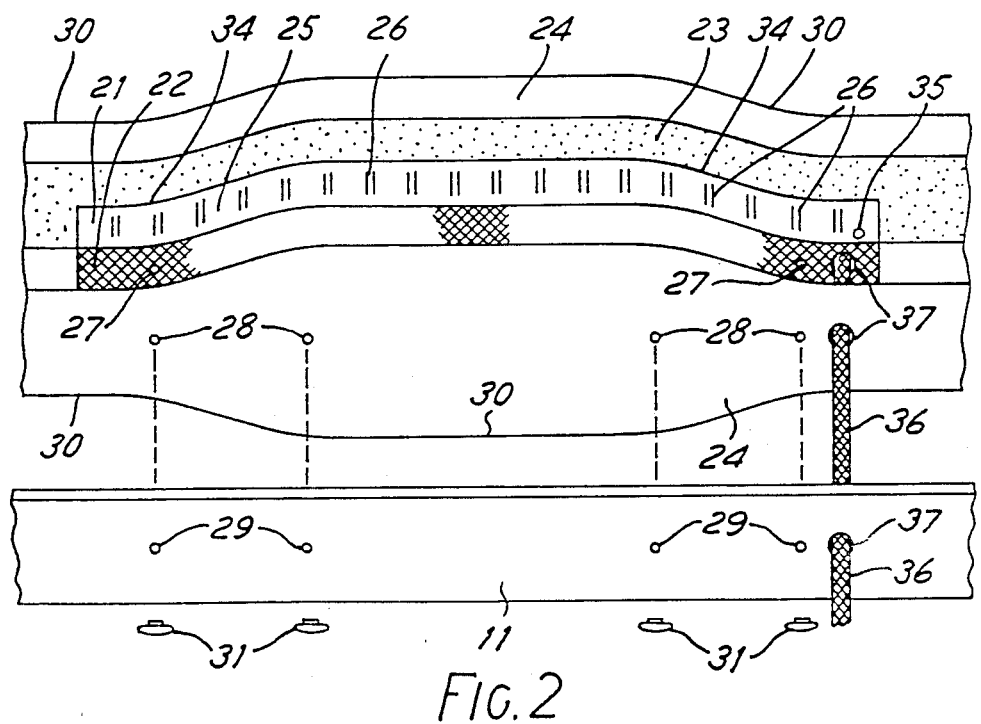
FIG. 2 is an expanded view of the inflatable support unit showing its constituent parts.

With reference to FIG. 2, the inflatable support padding means 12 of the therapeutic belt consists of an inflatable air bladder 21, support surface 22, padding means 23, and liner 24. The air fed into the air bladder 21 is directed into at least two intercommunicating cells 25, which in the present embodiment are arranged as longitudinally extending, laterally spaced-apart air cells separated by a plurality of ribs 26 which are parallel to each other and perpendicular to of the lateral axis of the belting means 11. The bladder 21 is secured to the the support surface 22 which can be constructed of any suitable semi-rigid material that is bendable when subjected to forces encountered thereby. Disposed against the bladder 21 on the side closest to the wearer is a padding means 23, which may be constructed of foam-like or any other suitable material. The liner material 24 is disposed so as to surround the bladder 21, support surface 22, and padding 23, and may be sewn or otherwise bonded around its entire perimeter 30. Fastening studs 27 may be disposed on the side of the support surface facing away from the wearer. Such studs 27 may protrude through holes 28 in the liner 24 and holes 29 in the belting material 11. Said studs 27 line up with the holes 28 in the liner 24 and the holes 29; in the belting material 11 and attach securely by means or rivet heads 31 or other suitable means. This method of construction allows for versatile attachment of the inflatable support padding means 12 to a variety of belt lengths. Such construction also allows for the ability to extend the padding means 23 at portions 33 beyond the length of the air bladder 21 on either side if the bladder to give added comfort to the wearer, particularly at the hips and ribs. In addition, FIG. 1 shows the disposition of additional padding 16 which may be disposed on the belt fastening means 13.

Returning to FIG. 2, the air bladder 21, which has capable of inflation, a substantially rectangular configuration, although said bladder may be tapered at its extremeties 34 or constructed to assume an oval shape in order to avoid interference with the wearer's hip and rib area so as to provide additional comfort. Fluid may be introduced into the bladder by means of a circular cavity 35 into which a tube 36 or other suitable means is attached and secured so as to effect a seal and provide a duct through which fluid can be transferred from a means such as an air pump device. The support surface 22, liner 24, and belting material 11 contain access holes 37 through which the tube 36 from the bladder extends and onto which an air pump is attached (see FIG. 4).

Figure 4:
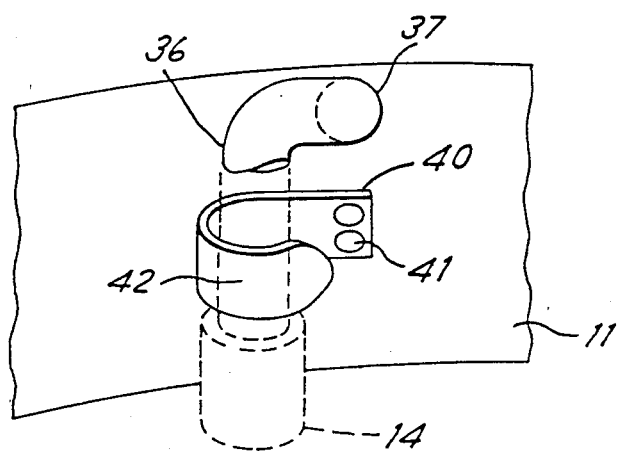
FIG. 4 is a perspective view of the air pump attachment means.

FIG. 4 shows the air pump attachment means 40, which can be secured to the belting material 11, by rivets 41, or other suitable fastening means. The air pump attachment means 40 is disposed on the belting material 11 directly below the access hole 37, through which the tube 36 from the air bladder extends. The air pump attachment means 40 consists of a "C" ring or spring clasp 42, which can be constructed from any suitable material having elastic properties such as plastic or stainless steel.

Figure 3A:
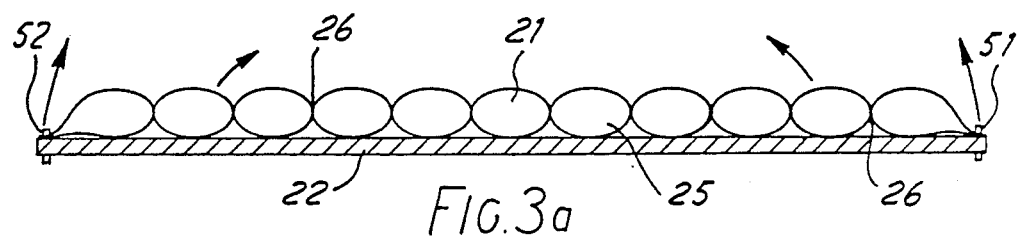
FIG. 3a is a perspective view of the inflatable bladder as attached to the support surface.
Figure 3B:
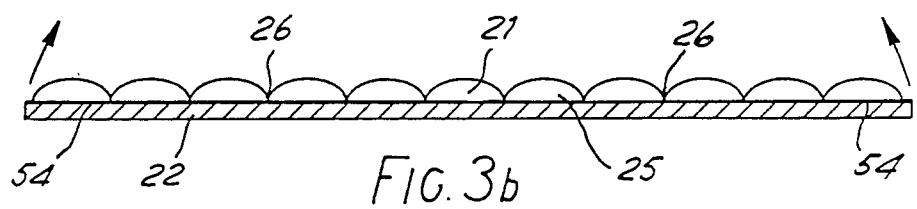
FIG. 3b is a perspective view of an alternative disposition of the inflatable bladder on the support surface.

FIGS. 3a and 3b show a perspective view of the inflatable air bladder 21 and its disposition on the support surface. The bladder 21 can be constructed of any material capable of holding compressed air or other fluid under pressure. The cell structure of the bladder comprising the intercommunicating cells 25 may be created by means of stitching the bladder material along certain lines forming the ribs 26 or other wise forming a bond of areas of contacts of the two opposing side of the bladder material so as to effect a suitable structure. The bladder may then be secured at both ends 51, 52 thereof to the inner support surface as shown in FIG. 3a. When the bladder is inflated without the individual air cells being attached to the support surface, as shown in FIG. 3a at 54, such attachment acts to pull the extremeties of inner support surface to deform it from a substantially flat planar surface to a concave surface having; a crescent shape in excess of 30° corresponding to the natural shape of the, human body at the sacro-lumbar area of the torso. The attachment only at the bladder ends permits each communicating air cell to inflate to its fullest potential. Utilizing this principle, FIG. 3b shows that attachment of the bladder to the support surface 22 by adhesion of one entire surface 54 will limit the amount of volume each air cell will assume while the whole unit curves naturally into a crescent shape. Thus, by choosing the exact method of attachment the amount of volume the air cells take up can be controlled. This allows for a reduction in bulk by means of the attachment method while maintaining the pressure equivalent of a non-attached bladder. Thus, as shown in FIGS. 3a and 3b, the air bladder 21 includes at least one surface which forms a plurality of recesses when the air bladder is inflated and each of the recesses is located between and adjacent pair of air cells 25.

If the air bladder 21 was not attached to the support surface 22, the sectioned bladder would shrink in length during inflation. Thus, the method of attachment of the bladder 21 to tne support surface 22 will dictate the degree of shrinkage and thus the ultimate shape of the thereapeutic belt upon full inflation.

FIG. 5 reveals the disposition of additional padding 61 which can be applied to the therapeutic belt appliance on the side next to the user for the purpose of providing more precise lateral counterpressure for controlling the stability of the sacro-lumbar region. In the embodiment shown in FIG. 5, a trapezoidal pad 71 can be applied to the padding means 23 at any point for the purpose of "filling" the contours of the back, thus assuring total contact and, where necessary, the application of additional counterpressure to provide needed support.

FIG. 6 shows some additional embodiments of various padding means 73, 74, and 75, which are capable of being incorporated onto the therapeutic belt appliance by means of a liner or other suitable methods of attachment. Said padding means can be inflated separately or along with the preferred bladder, thus permitting the flexibility of applying support at various pressures as necessary. While the present invention has been described with reference to the foregoing embodiments, it will be understood by those skilled in the art that various changes and modifications can be made therto without departing from the scope of the claimed invention.

I claim:

1. An inflatable therapeutic belt-type appliance suitable for treating the sacro-lumbar region of a person's body, comprising:
   belt means extending in a lateral direction for securing said therapeutic belt-type appliance about the abdominal region of a person's body, said belt means including an inner surface adapted to face the person's body when in place therearound;
   means disposed on said belt means for causing said belt means to bow in an arcuate manner when said therapeutic appliance is inflated so that said inner surface of said belt means is deformed from a substantially flat planar surface when said therapeutic device is not inflated to a concave surface when said therapeutic device is inflated, said means comprising an air bladder secured to said belt means and adapted to apply pressure to the sacro-lumbar region of a person's body when said appliance is inflated and said belt means is secured around the abdominal region of the person's body, said air bladder including a plurality of air cells, each of said air cells extending longitudinally in a direction perpendicular to said lateral direction and being spaced apart from each other in said lateral direction, said air cells expanding to shrink said air bladder when said air bladder is inflated to thereby cause said inner surface of said belt means to deform from said substantially flat planar surface when said air cells are not inflated to said concave surface when said air cells are inflated; and
   means disposed on said belt means for supplying fluid to said air bladder whereby said air cells can be inflated.

2. The inflatable therapeutic belt-type appliance of claim 1, wherein said air bladder is disposed on said inner surface of said belt means.

3. The inflatable therapeutic belt-type appliance of claim 1, further comprising a semi-rigid support surface between said inner surface of said belt means and said air bladder.

4. The inflatable therapeutic belt-type appliance of claim 1, wherein said air bladder includes opposite ends thereof spaced apart in said lateral direction, said air bladder having a width in a direction perpendicular to said lateral direction which becomes smaller towards said opposite ends of said air bladder to thereby contour said air bladder to avoid a hip and a rib area of a user of said therapeutic appliance.

5. The inflatable therapeutic belt-type appliance of claim 1, further comprising liner means disposed around said belt means and said air bladder for forming a module unit.

6. The inflatable therapeutic belt-type appliance of claim 1, wherein said air bladder includes a surface facing said belt means, said surface of said air bladder being secured to said belt means along the entire length in said lateral direction of said air bladder.

7. The inflatable therapeutic belt-type appliance of claim 1, wherein at least one surface of said air bladder is corrugated and forms a plurality of recesses when said air bladder is inflated, each of said recesses being between an adjacent pair of said air cells.

8. The inflatable therapeutic belt-type appliance of claim 1, wherein said means for supplying fluid to said air bladder comprises an air tube connected to said air bladder and said belt means further includes a spring clasp which detachably secures a free end of said air tube to said belt means.

9. The inflatable therapeutic belt-type appliance of claim 1, further comprising padding means disposed on said belt means for providing comfort to the user of said therapeutic appliance, said air bladder being disposed between said belt means and said padding means.

10. The inflatable therapeutic belt-type appliance of claim 9, further comprising additional padding means disposed on said belt means for providing more precise counterpressure to the sacro-lumbar region of a person wearing said therapeutic belt-type appliance, said additional padding means comprising at least one inflatable pad connected to a means for supplying fluid thereto.

11. The inflatable therapeutic belt-type appliance of claim 1, wherein said air cells are separated by a plurality of ribs formed in said air bladder, said ribs being substantially parallel to each other and extending in a direction perpendicular to said lateral direction with one of said ribs located between each adjacent pair of said air cells.

12. The inflatable therapeutic belt-type appliance of claim 11, wherein said ribs comprise areas of contact between opposing sides of said air bladder.

13. An inflatable therapeutic belt-type appliance for treating the sacro-lumbar region of a person's body, comprising:

belt means extending in a lateral direction for securing said therapeutic belt-type appliance about the abdominal region of a person's body, said belt means including an inner surface adapted to face the person's body when in place therearound;

means disposed on said belt means for causing said belt means to bow in an arcuate manner when said therapeutic appliance is inflated so that said inner surface of said belt means is deformed from a substantially flat planar surface when said therapeutic device is not inflated to a concave surface when said therapeutic device is inflated, said means comprising an air bladder secured to said belt means and adapted to apply pressure to the sacro-lumbar region of a person's body when said appliance is inflated and said belt means is secured around the abdominal region of the person's body, said air bladder including a plurality of air cells, each of said air cells extending longitudinally in a direction perpendicular to said lateral direction and being spaced apart from each other in said lateral direction, said air cells expanding to shrink said air bladder when said air bladder is inflated to thereby cause said inner surface of said belt means to deform from said substantially flat planar surface when said air cells are not inflated to said concave surface when said air cells are inflated, said air bladder including opposite ends spaced apart in said lateral direction, said air bladder being secured to said belt means only at said opposite ends of said air bladder; and means disposed on said belt means for supplying fluid to said air bladder whereby said air cells can be inflated.

* * * * *